(12) United States Patent
Lee

(10) Patent No.: US 12,064,219 B2
(45) Date of Patent: Aug. 20, 2024

(54) DETERMINING BLOOD PULSE CHARACTERISTICS BASED ON STETHOSCOPE DATA

(71) Applicant: International Business Machines Corporation, Armonk, NY (US)

(72) Inventor: Kang-Wook Lee, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 707 days.

(21) Appl. No.: 17/136,444

(22) Filed: Dec. 29, 2020

(65) Prior Publication Data
US 2021/0113102 A1    Apr. 22, 2021

Related U.S. Application Data

(63) Continuation of application No. 15/841,507, filed on Dec. 14, 2017, now Pat. No. 10,939,830, which is a
(Continued)

(51) Int. Cl.
*A61B 5/021* (2006.01)
*A61B 5/02* (2006.01)
(Continued)

(52) U.S. Cl.
CPC ...... *A61B 5/02125* (2013.01); *A61B 5/02028* (2013.01); *A61B 5/0205* (2013.01);
(Continued)

(58) Field of Classification Search
CPC ............ A61B 5/02125; A61B 5/02028; A61B 5/0205; A61B 5/0456; A61B 5/0452;
(Continued)

(56) References Cited

U.S. PATENT DOCUMENTS 9,101,275 B2    8/2015    Thakur et al.
9,408,542 B1    8/2016    Kinast et al.
(Continued)

OTHER PUBLICATIONS

Sotera Wireless, "ViSi Mobile Surveillance Monitoring System," 2016 Sotera Wireless, 6 pages.
(Continued)

*Primary Examiner* — Devin B Henson
(74) *Attorney, Agent, or Firm* — Amin, Turocy & Watson, LLP

(57) ABSTRACT

Techniques for determining pulse transit time (PTT) and blood pressure measurements based on stethoscope data are provided. In one example, a system comprises a stethoscope component that monitors a heart and generates stethoscope data representative of a sound wave generated by the heart. The system can further comprise an analysis component that receives the stethoscope data and receives, from a photoplethysmography (PPG) component that monitors an extremity, PPG data representative of a pulse wave at the extremity. The analysis component can determine, based on the stethoscope data, a first time corresponding to closure of a tricuspid valve of the heart and can determine a PTT as a function of the first time and a second time corresponding to the pulse wave at the extremity that is determined based on the PPG data. Blood pressure measurements can be obtained from algorithms with the inputs of PTT or times determined based on the PPG data.

11 Claims, 10 Drawing Sheets

Related U.S. Application Data continuation of application No. 15/423,308, filed on Feb. 2, 2017, now Pat. No. 10,932,676.

(51) Int. Cl.

| | | |
|---|---|---|
| *A61B 5/0205* | (2006.01) | |
| *A61B 5/0245* | (2006.01) | |
| *A61B 5/349* | (2021.01) | |
| *A61B 5/352* | (2021.01) | |
| *A61B 7/00* | (2006.01) | |
| *A61B 7/04* | (2006.01) | |
| *A61B 5/024* | (2006.01) | |
| *A61B 5/11* | (2006.01) | |

(52) U.S. Cl.
CPC .............. *A61B 5/349* (2021.01); *A61B 5/352* (2021.01); *A61B 7/00* (2013.01); *A61B 7/04* (2013.01); *A61B 7/045* (2013.01); *A61B 5/02405* (2013.01); *A61B 5/02416* (2013.01); *A61B 5/02427* (2013.01); *A61B 5/02438* (2013.01); *A61B 5/0245* (2013.01); *A61B 5/1102* (2013.01); *A61B 2562/0204* (2013.01)

(58) Field of Classification Search
CPC ............ A61B 5/02405; A61B 5/02416; A61B 5/0245; A61B 5/1102; A61B 7/04; A61B 7/045

See application file for complete search history.

(56) References Cited

U.S. PATENT DOCUMENTS

| | | |
|---|---|---|
| 2008/0082004 A1 | 4/2008 | Banet et al. |
| 2008/0214942 A1 | 9/2008 | Oh et al. |
| 2009/0211838 A1 | 8/2009 | Bilan |
| 2016/0220122 A1 | 8/2016 | Luna et al. |
| 2017/0281024 A1 | 10/2017 | Narasimhan et al. |
| 2017/0340209 A1 | 11/2017 | Klaassen et al. |

OTHER PUBLICATIONS

Caretaker Medical, "Caretaker: the Worlds Most Innovative Wireless Patient Monitor," http://www.caretakermedical.net/caretaker/, 2016, 3 pages.

Metz, "Health-Tracking Startup Fails to Deliver on its Ambitions," https://www.technologyreview.com/s/601029/health-tracking-startup-fails-to-deliver-on-its-ambitions/, Mar. 15, 2016, 5 pages.

Fung, et al., "Continuous Noninvasive Blood Pressure Measurement by Pulse Transit Time," Proceedings of the 26th Annual International Conference of the IEEE EMBS, Sep. 1-5, 2004, 4 pages.

Yoon, et al., "Non-Constrained Blood Pressure Monitoring using ECG and PPG for Personal Healthcare", J Med Syst (2009) 33: pp. 261-266.

Gesche, et al., "Continuous blood pressure measurement by using the pulse transit time: comparison to a cuff-based method", Eur J Appl Physiol, (2012), pp. 309-315.

Fuke, et al., "Blood pressure estimation from pulse wave velocity measured on the chest," 35th Annual Intl Conf of the IEEE EMBS; Osaka, Japan; Jul. 3-7, 2013, 4 pages.

Lee, et al., "Wearable Blood Pressure Monitoring System," U.S. Appl. No. 15/269,040, filed Sep. 19, 2016, 29 pages.

Lee, "Combined Wearable Electrocardiogram and Electronic Stethoscope," U.S. Appl. No. 15/274,574, filed Sep. 23, 2016, 35 pages.

Kim, et al., "Ballistocardiogram as Proximal Timing Reference for Pulse Transit Time Measurement: Potential for Cuffless Blood Pressure Monitoring," IEEE Transactions on Biomedical Engineering, vol. 62, No. 11 Nov. 2015, 8 pages.

Mukkamala, et al., "Toward Ubiquitous Blood Pressure Monitoring via Pulse Transit Time: Theory and Practice," IEEE Transactions on Biomedical Engineering, vol. 62, No. 8, Aug. 2015, 23 pages.

Griggs, et al., "Design and Development of Continuous Cuff-less Blood Pressure Monitoring Devices," IEEE, 2016, 3 pages.

List of IBM Patents and Applications treated as related.

Non-Final Office Action received for U.S. Appl. No. 15/423,308 dated Jun. 24, 2019, 34 pages.

Final Office Action received for U.S. Appl. No. 15/423,308 dated Nov. 19, 2019, 28 pages.

Non-Final Office Action received for U.S. Appl. No. 15/841,507 dated Apr. 22, 2020, 33 pages.

Non-Final Office Action received for U.S. Appl. No. 15/423,308 dated May 20, 2020, 38 pages.

Final Office Action received for U.S. Appl. No. 15/841,507 dated Aug. 17, 2020, 26 pages.

Notice of Allowance received for U.S. Appl. No. 15/841,507 dated Nov. 4, 2020, 12 pages.

Notice of Allowance received for U.S. Appl. No. 15/423,308 dated Oct. 29, 2020, 14 pages.

DETERMINING BLOOD PULSE CHARACTERISTICS BASED ON STETHOSCOPE DATA

BACKGROUND

The subject disclosure relates to techniques for determining blood pulse characteristics, and more specifically, to determining blood pulse characteristics based on stethoscope data.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate determination of blood pulse characteristics based on stethoscope data.

According to an embodiment, a system is provided. The system can comprise a memory that stores computer executable components and a processor that executes computer executable components stored in the memory. The computer executable components can comprise a stethoscope component that monitors a heart and generates stethoscope data representative of a sound wave generated by the heart. The system can further comprise an analysis component coupled to the stethoscope component and that receives the stethoscope data and receives, from a photoplethysmography (PPG) component that monitors an extremity, PPG data representative of a pulse wave at the extremity. The analysis component can determine, based on the stethoscope data, a first time corresponding to closure of a tricuspid valve of the heart and can determine a pulse transit time (PTT) as a function of the first time and a second time corresponding to the pulse wave at the extremity that is determined based on the PPG data.

In various embodiments, elements described in connection with the system can be embodied in different forms such as a computer-implemented method, a computer program product, or another form.

DETAILED DESCRIPTION

Figure 1:
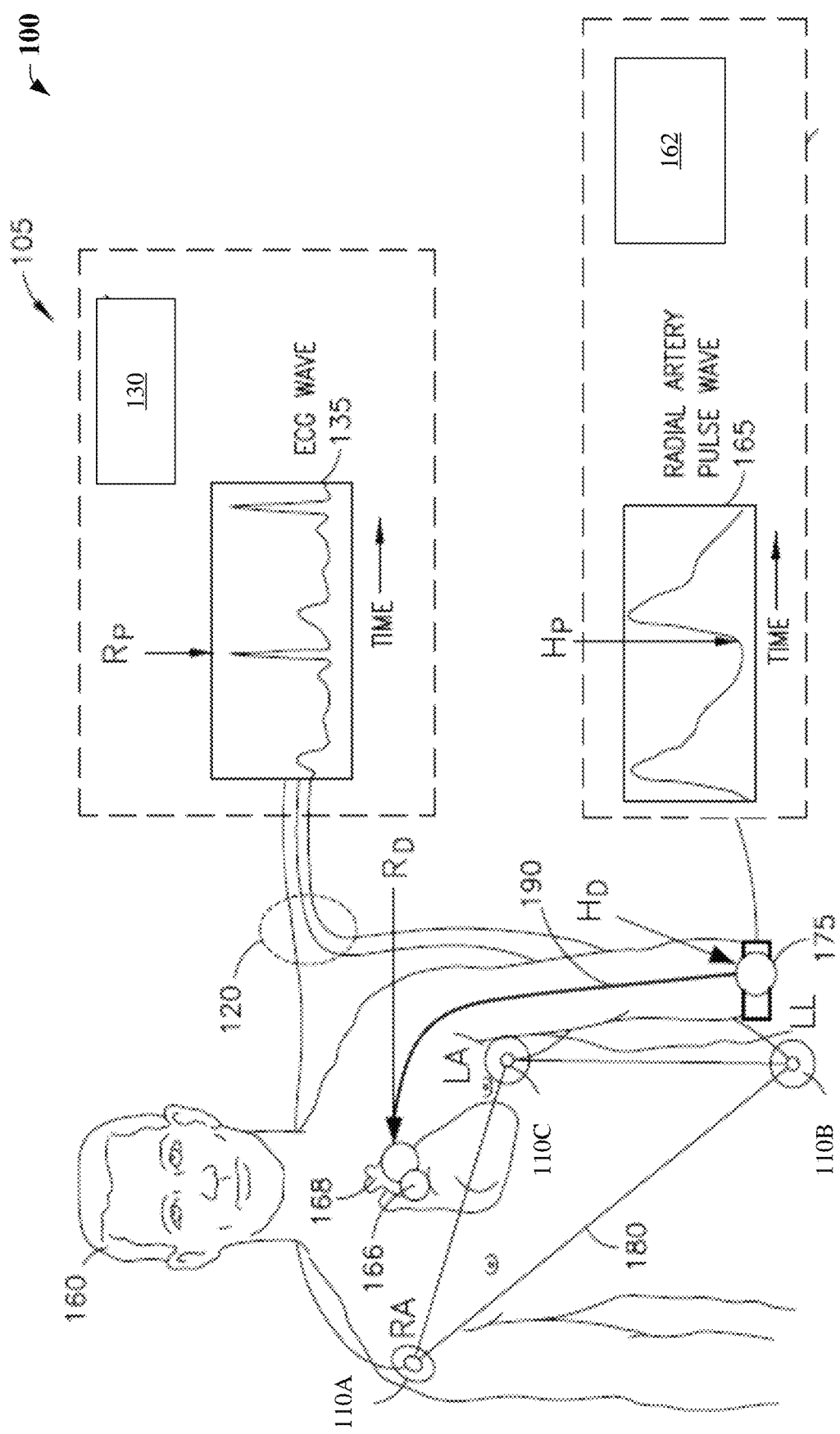
FIG. 1 illustrates a block diagram of an example, non-limiting system that can facilitate determination of blood pulse characteristics in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

This disclosure relates in some embodiments to determining characteristics associated with a heart or pulse based on stethoscope data. Examples of the aforementioned characteristics that can be determined can be a PTT or BP measurements and/or estimations.

As used herein, the term "PTT" is intended to refer to an amount of time for a pulse pressure wave to propagate through a length of an arterial tree of the body of a patient. One example of an arterial tree can be the portion of the artery from the heart to an extremity (e.g., arm) of the body. The pulse pressure wave can result from the ejection of blood from the left ventricle of a heart, which can move with a velocity generally much greater than the forward movement of the blood. It is generally assumed that blood is ejected from the left ventricle when the aortic valve of the heart opens. Hence, in one or more embodiments described herein, PT can represent the difference between a first time at which the aortic valve opens and a second time at which the pressure wave arrives at the extremity. It is to be understood that the discussion of time described herein can represent an exact time or an approximate time within a defined acceptable range.

PTT can be estimated in a variety of ways. Perhaps the most common technique is based on electrocardiography (ECG). ECG devices record the electrical activity of the heart of a patient over a time based on data received from various electrodes placed on the skin of the patient. The electrodes detect the small electrical changes on the skin that occur in response to the heart muscle electrophysiological pattern of depolarizing during a cardiac cycle. The biggest peak of the electrical charge during a cardiac cycle is referred to as the R peak. Because it can take time to transfer an electrical signal to the heart muscle motion, the R peak time tends to differ slightly from the time at which the aortic valve opens. In other words, there can be a small but significant difference between the opening of the aortic valve and R peak. In some embodiments, that delay is not small enough to ignore. However, as long as the delay between aortic valve opening and R peak is consistent, certain measurements such as T, blood pressure, or the like can be calculated or estimated using algorithms since constants of the algorithms can be determined on the basis of the consistent delay. For example, algorithms with determined constants that account for the consistent delay can be employed. If the delay is not consistent, such algorithms, with defined constants, may yield unsuitable results. Hence, when estimating PIT, the time at which the R peak occurs can be used as a basis for estimating the time at which the aortic valve opens. For example, this R peak time can be compared to data from other electrodes of the ECG device or to data from a PPG device that can detect when the pressure wave reaches the extremity.

However, in some cases, such as when the patient has an aortic regurgitation, a heart murmur, or another condition, the time at which an ECG device measures the R peak value may not provide a proper basis for determining the aortic valve opening. For example, if the delay between R peak and aortic valve opening is not consistent, algorithms that presume a consistent delay may be inaccurate. In such situations, ECG data will not provide an accurate PTT. As one result, a BP measurement, which is typically determined as a function of the PIT, will be inaccurate as well.

Blood pressure measurements represent one of the most important pieces of data in connection with health and wellness. For example, BP measurements can be used for detection of an early onset condition, assessing recovery from a medical intervention, and many others. Outside of the intensive care unit (ICU), most vital signs, such as BP, are only checked two to four times a day. Thus, substantial benefits can be provided by devices that are capable of constantly monitoring as well as ensuring that BP measurements are accurate, even in cases in which ECG measurements may not have sufficient accuracy because assumptions about the difference between R peak and aortic valve opening are not valid.

One or more embodiments described herein relate to a stethoscope device such as an electronic stethoscope or an electronic visible stethoscope that can monitor a heart. Based on said monitoring, an analysis device can determine when a tricuspid valve of the heart closes, for example based on the data generated by the stethoscope device that is detected based on the sound of the tricuspid valve closing. It can be assumed that closure of the tricuspid valve coincides with opening of the aortic valve. Thus, with the stethoscope data and suitable data from a PPG device that monitors the pulse pressure wave at an extremity, the analysis device can determine PTT. Other ECG techniques assume the aortic valve opens at R peak, which is determined based on electrical charge data. One or more embodiments described herein can assume opening of the aortic valve can be estimated based on the time of R peak, which is determined based on electrical charge data. However, one or more other embodiments can additionally or alternatively rely on a further observation that the aortic valve opening corresponds to the tricuspid valve closing, which can be determined based on sound and/or mechanical wave data received from a stethoscope.

Once PTT is determined, in one or more embodiments, a systolic BP value can be determined as a function of the PT. Additionally, a diastolic BP value can be determined as a function of the systolic BP value or the values of the pulse wave. In some embodiments, such can be similar to techniques used by previous ECG systems, even though previous ECG systems differ in the determination of PTT in some instances.

While in some embodiments, the stethoscope data can be used instead of ECG data, in other embodiments, both stethoscope data and ECG data can be used. For example, both ECG data and stethoscope data can be collected and analyzed. One or the other type of data can be used to determine PTT based on various factors including, but not limited to, selecting the data source that is determined to be more accurate. For example, ECG data can be used to calculate PTT unless ECG data indicates (e.g., by stethoscope data) that R peak of the ECG data is not representative of aortic valve opening. In that embodiment, stethoscope data can be utilized instead of ECG data to determine PTT and/or BP measurement. In some embodiments, both ECG data and stethoscope data can be used collectively, for example to provide a PTT that is more precise than the T value determined by either data type alone.

Turning now to the drawings, FIG. 1 illustrates a block diagram of an example, non-limiting system that can facilitate determination of blood pulse characteristics in accordance with one or more embodiments described herein. System 100 and/or the components of the system 100 or other systems disclosed herein (e.g., system 500) can be employed to use hardware and/or software to solve problems that are highly technical in nature, that are not abstract, and that cannot be performed as a set of mental acts by a human. Further, some of the processes performed can be performed by specialized computers or devices for carrying out defined tasks related to obtaining and transforming data relating to physical phenomena and/or biological processes. Those processes that specialized computers and/or devices can carry out can include, but are not limited to, generation of stethoscope data representative of a sound wave generated by the heart, processing of PPG data representative of a pulse wave at the extremity and/or determination of a PTT based on the PPG data. System 100 and/or components of system 100 or other systems described herein can be employed in some embodiments to solve new problems that arise through advancements in technology, computer networks, the Internet, and the like such as getting improved BP data. System 100 or other systems detailed herein can provide technical improvements in accurate and/or persistent estimation of one or both PIT and BP. Generally, systems 100, 500, and other systems detailed herein as well as individual components detailed herein can comprise a processor and a memory that stores executable instructions that, when executed by the processor, facilitate performance of operations. Examples of the memory and processor can be found with reference to FIG. 10.

As noted previously, it is possible to provide an estimate of BP for a patient (e.g., a human or animal) by using data from an electrocardiogram (ECG) device and at least one PPG device or sensor in accordance with one or more embodiments of the disclosed subject matter. For example, the PPG device can be implemented as an oximeter.

Still referring to FIG. 1, this figure illustrates a system 100 that can be used on a patient 160 to determine information that can be used for an estimate of BP. Patient 160 is also referred to as a person or human being herein, but it is understood that the disclosed techniques may be applied to other organisms. In the embodiment shown, the ECG sensor 105 can comprise ECG circuitry 130, wiring 120, and three electrodes 110A, 110B, and 110C. Electrode 110A is positioned on the right arm (RA), electrode 110B is positioned on the left lower (LL) arm, and electrode 110C is positioned on the left upper arm (LA) in these embodiments, but other embodiments with other arrangements are possible. The electrodes 110 are formed in a triangle 180 in this example. While this triangle embodiment is shown in FIG. 1, other possible embodiments are also envisioned. For example, in some embodiments, a different number of electrodes 110 can be applied to patient 160 and/or may be placed at other locations of patient 160.

The ECG circuitry 130 of ECG sensor 105 can generate ECG wave data 135, which can be data describing electrical signals from the heart 168 and can be in units of millivolts over time. ECG wave data 135 can be generated using electrical signal information collected by the electrodes 110. Such information can be received by ECG sensor 105 from electrodes 110 via wiring 120 that can couple electrodes 110 to ECG sensor 105. In some embodiments, wiring 120 is optional and information from electrodes 110 can be received wirelessly. Also shown is a PPG sensor 175, which can include PPG circuitry 162. In some embodiments, the PPG sensor 175 can be an oximeter sensor with oximeter circuitry. The PPG circuitry 162 can generate radial artery pulse wave data 165 based on blood flow in the artery. A PPG unit (e.g., PPG sensor 175) can determine relative blood absorbance versus time, which can also indicate relative blood volume versus time. An oximeter unit can determine a percentage of oxygen saturation in the artery. Here, $R_P$, $R_D$, $H_P$, and $H_D$ are the maximum R peak of the ECG wave data 135, the distance of aortic valve position, the starting point of radial artery pulse wave data 165, and the distance of radial wrist position, respectively. In addition, the circle 166 and the solid line 190 respectively represent a position of the aortic valve and the approximate distance from aortic valve to wrist, where PPG sensor 175 is situated.

In some embodiments, electrodes 110, or other components detailed herein, can comprise a number of leads (e.g., about two or three leads) that can be placed in a single patch with a circular, rectangular, or other shape. In some embodiments, the patch can be have a length or diameter of about 20-50 mm. In some embodiments, the patch, ECG sensor 105, or other elements or components detailed here can be wearable elements, components, or devices. In some embodiments, the elements, components, or devices detailed herein can communicate wirelessly.

Figure 2:
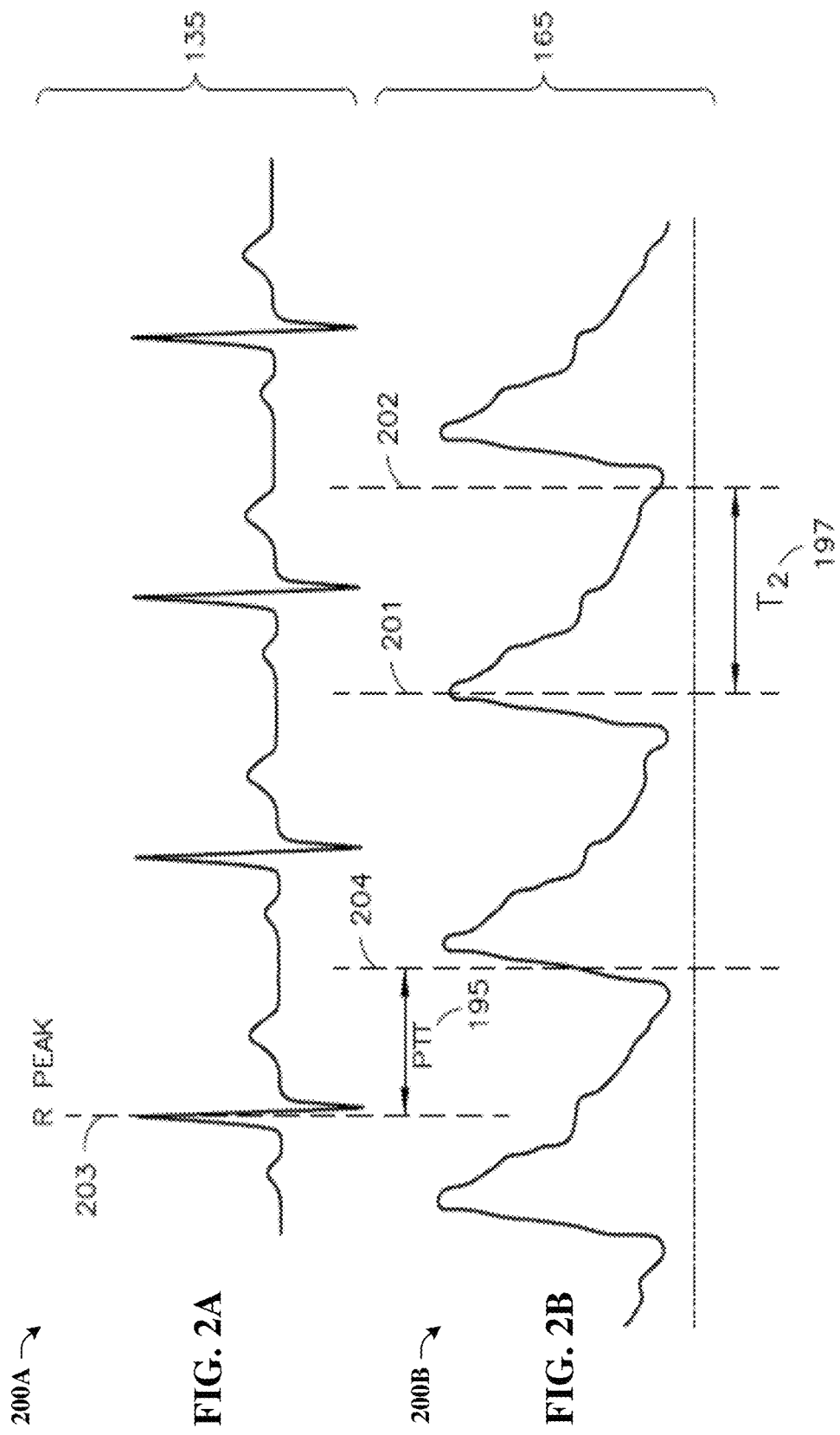
FIG. 2A illustrates a graphical representation of a non-limiting example of an electrocardiography (ECG) wave data graph in accordance with one or more embodiments described herein.
FIG. 2B illustrates a graphical representation of a non-limiting example of a radial artery pulse wave data graph in accordance with one or more embodiments described herein.

FIG. 2A illustrates a graphical representation 200A of a non-limiting example of an electrocardiography (ECG) wave data graph in accordance with one or more embodiments described herein. FIG. 2B illustrates a graphical representation 200B of a non-limiting example of a radial artery pulse wave data graph in accordance with one or more embodiments described herein. In these examples, graphical illustrations 200A and 200B are on the same time scale. Repetitive description of like elements employed in other embodiments described herein is omitted for sake of brevity.

Regarding graphical illustration 200B, this particular exemplary radial artery pulse wave data 165 can be determined using the PPG data detailed in connection with FIG. 1. For example, by monitoring at an extremity (e.g., a wrist of patient 160), appropriate PPG data can be generated. In some embodiments, certain types of PPG data, other than or in addition to radial artery pulse wave data 165 can also be determined based on one or more pressure sensors. PTT can be determined by comparing the R peak 203 of the ECG wave data 135 and a corresponding inclination (e.g., maximum inclination 204) of the radial artery pulse wave data 165. In some embodiments, R peak 203 can correspond to $R_P$ illustrated in connection with ECG wave data 135 of FIG. 1. The time represented as $T_2$ 197 can be representative of a time interval between the peak point 201 of a pulse wave and the baseline point 202 where the pulse wave reaches the baseline.

Figure 3:
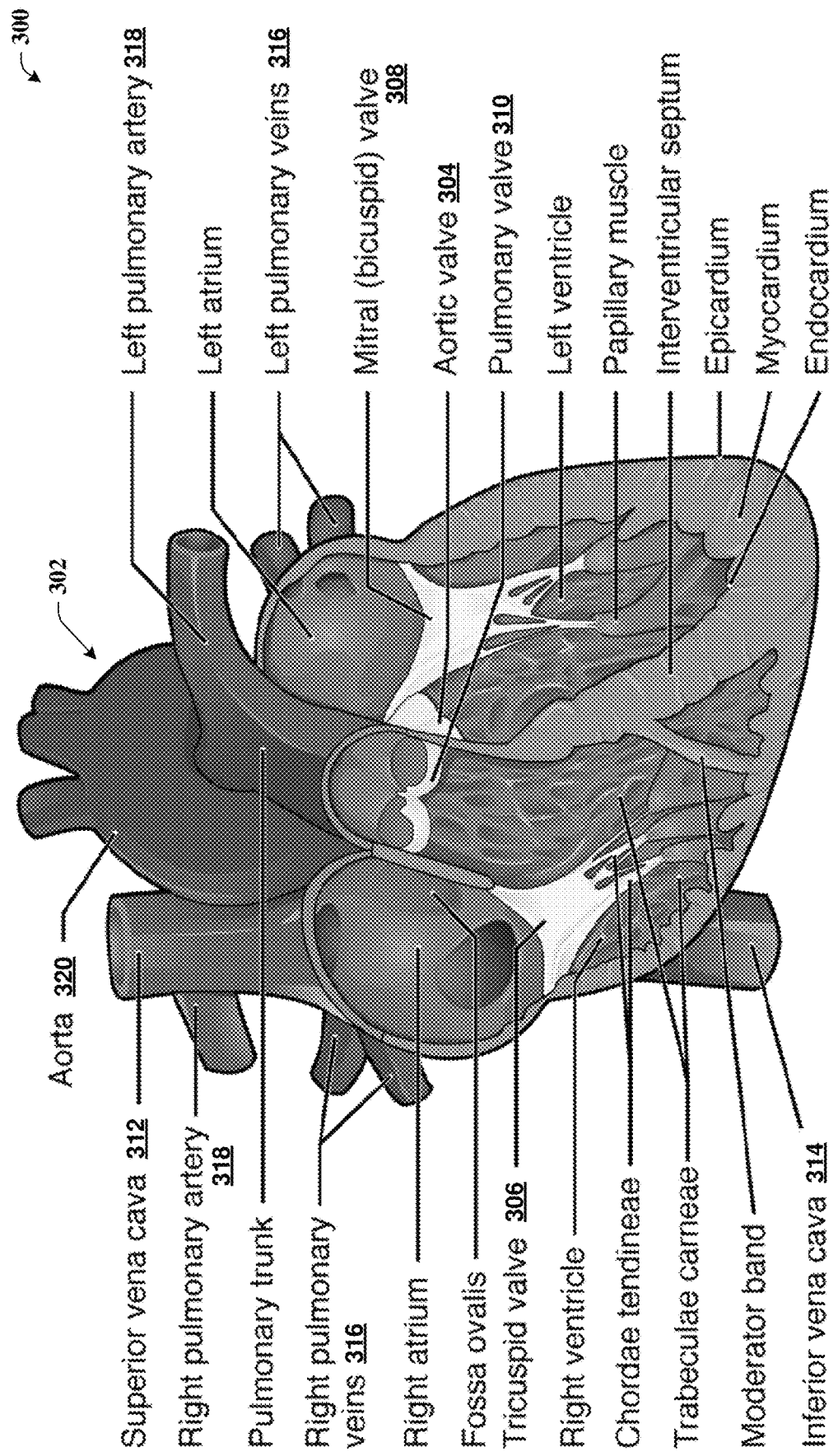
FIG. 3 illustrates a graphical representation of a non-limiting example of a heart and corresponding blood flow in accordance with one or more embodiments described herein.

With reference now to FIG. 3, depicted is graphical representation 300. FIG. 3 illustrates a graphical representation 300 of a non-limiting example of a heart and corresponding blood flow in accordance with one or more embodiments described herein. Repetitive description of like elements employed in other embodiments described herein is omitted for sake of brevity. In one or more embodiments, heart 302 can be substantially similar in structure and/or operation to heart 168 of FIG. 1.

During a cardiac cycle, blood can enter the heart 302 at one or more locations (e.g., superior vena cava 312, inferior vena cava 314, pulmonary veins 316) shown in FIG. 3 and can exit the heart 302 at one or more other locations (e.g., pulmonary arteries 318, aorta 320) shown in FIG. 3. As has been discussed, estimations of PTT and/or BP can rely on a time at which the blood leaves heart 302, which occurs when aortic valve 304 opens. However, detecting when the aortic valve 304 opens can be difficult. ECG devices, for example, often endeavor to determine when depolarization of ventricle muscle cells occurs, which is assumed to coincide with the opening of aortic valve 304.

As detailed herein, in one or more embodiments, another way of determining or estimating when aortic valve 304 opens is to employ the evaluation of one or more mechanical waves such as sound waves in contrast to electrical signals detected by some ECG devices. Evaluation of one or more mechanical waves can be accomplished by utilizing a stethoscope component (e.g., stethoscope component 502), which is further detailed in connection with FIG. 5.

During a cardiac cycle, a typical sequence that can be detected by a stethoscope, in order, comprises: closure of the mitral valve 308, closure of the tricuspid valve 306, closure of the aortic valve 304, and closure of the pulmonary valve 310. While it may not be feasible in some instances to use sound to detect a valve opening, it is assumed herein that opening of aortic valve 304 substantially coincides with closure of the tricuspid valve 306. Thus, determining F can be accomplished by utilizing stethoscope data indicative of closure of the tricuspid valve 306 to represent opening of the aortic valve 304. Moreover, relying on R peak to estimate opening of the aortic valve 304, as is the case with some ECG devices, can lead to inaccurate F estimates as further detailed in connection with FIGS. 4A and 4B.

Figure 4A:
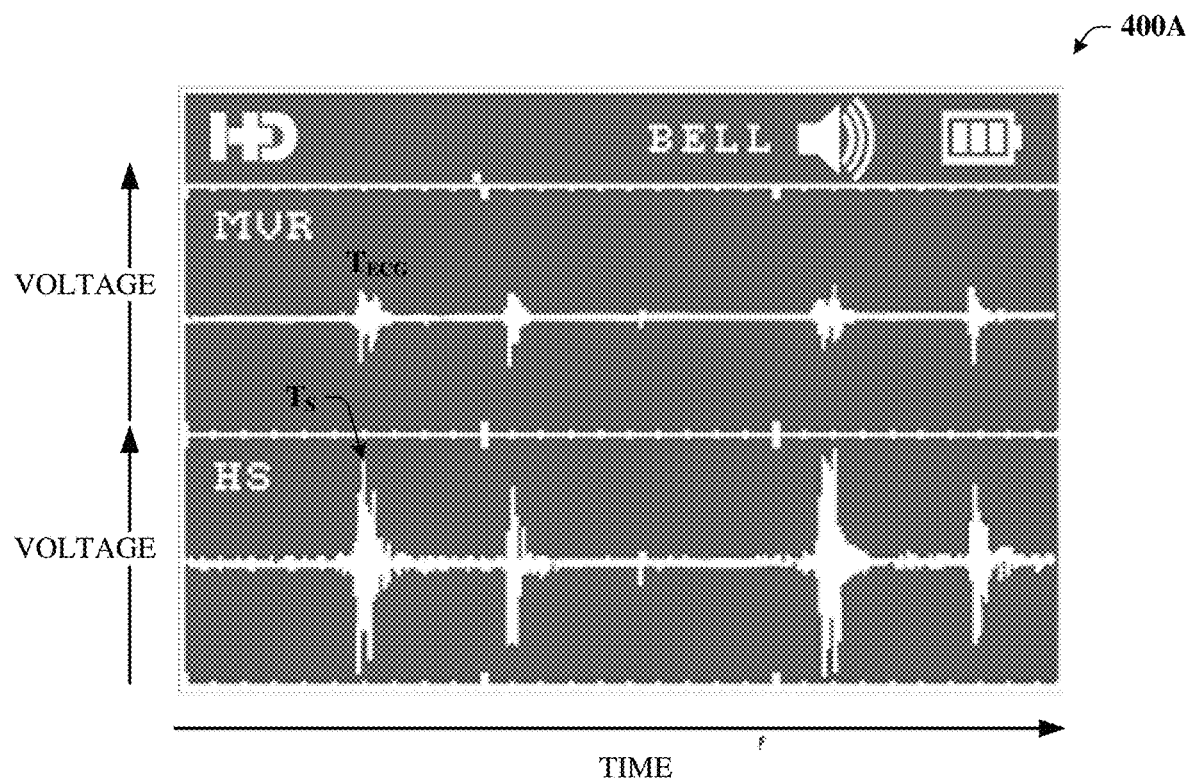
FIG. 4A illustrates a non-limiting example graphical representation of stethoscope data for normal cardiac cycles in accordance with one or more embodiments described herein.
Figure 4B:
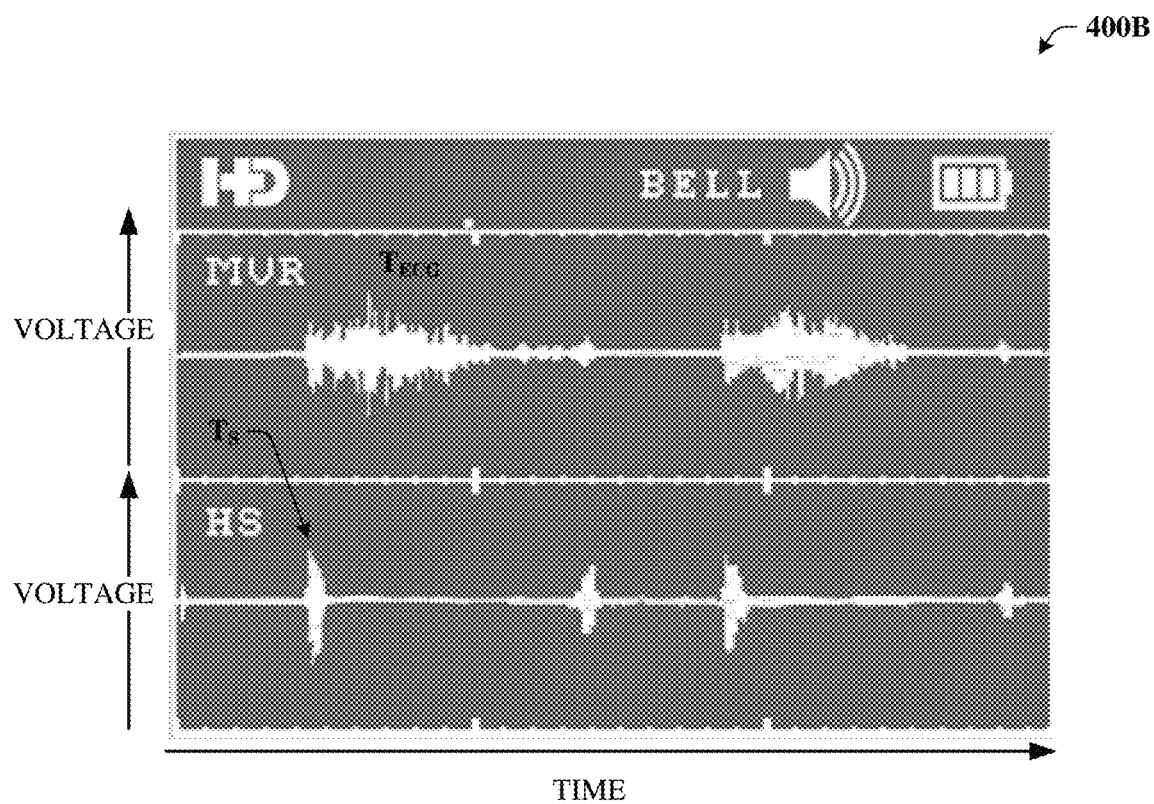
FIG. 4B illustrates a non-limiting example graphical representation of stethoscope data for cardiac cycles with an aortic regurgitation in accordance with one or more embodiments described herein.

Referring now to FIGS. 4A and 4B graphical representations 400A and 400B are depicted. FIG. 4A illustrates a non-limiting example graphical representation 400A of stethoscope data for normal cardiac cycles in accordance with one or more embodiments described herein. Repetitive description of like elements employed in other embodiments described herein is omitted for sake of brevity.

In this example, $T_S$ represents a time at which it is determined that the tricuspid valve 306 closes. Thus time $T_S$ can coincide with the opening of the aortic valve 304, which can indicate a start time for calculating PT. Since this example represents a normal heart, if ECG data were displayed on the same time scale, then it is likely that a time, $T_{ECG}$, at which the opening of the aortic valve (e.g., based on R peak) is determined, will be approximately the same as $T_S$. In such cases, both stethoscope data and ECG data can provide accurate PTT estimations.

FIG. 4B illustrates a non-limiting example graphical representation 400B of stethoscope data for cardiac cycles with an aortic regurgitation in accordance with one or more embodiments described herein. Repetitive description of like elements employed in other embodiments described herein is omitted for sake of brevity.

In this example, $T_S$ can represent a time at which it is determined that the tricuspid valve 306 closes. Such can coincide with opening of the aortic valve 304, which can represent a start time for calculating PT. Since this example represents an abnormal heart, if ECG data were displayed on the same time scale, then it is likely that a time, $T_{ECG}$, at which aortic valve opening is estimated will not coincide with $T_S$. In such cases, ECG data can result in inaccurate F estimations. As indicated previously, if determinations are not accurate, then BP calculations, which can be a function of T, will be inaccurate as well.

Figure 5:
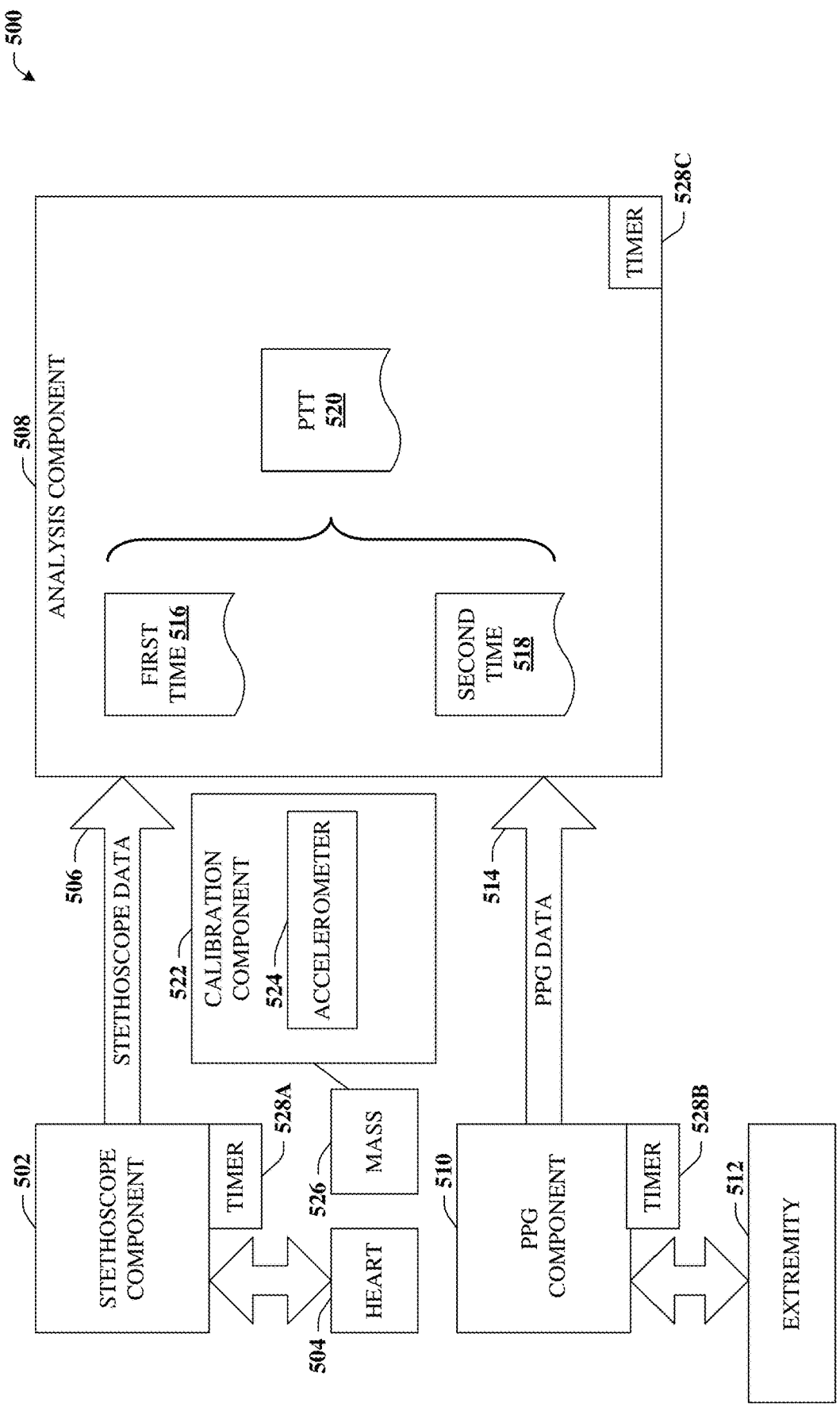
FIG. 5 illustrates a non-limiting example of a block diagram of a system that can facilitate determination of PTT based on stethoscope data in accordance with one or more embodiments described herein.

Turning now to FIG. 5, system 500 is depicted. FIG. 5 illustrates a non-limiting example of a block diagram of a system 500 that can facilitate determination of FT based on stethoscope data in accordance with one or more embodiments described herein. Repetitive description of like elements employed in other embodiments described herein is omitted for sake of brevity.

System 500 can comprise a stethoscope component 502 that can monitor a heart 504. Heart 504 can be representative of or substantially similar to the structure and/or function of heart 168 of FIG. 1 and/or heart 302 of FIG. 3. Based on the aforementioned monitoring of heart 504, stethoscope component 502 can generate stethoscope data 506. For example, stethoscope data 506 can be representative of a sound (e.g., mechanical) wave produced by heart 504 in the course of one or more cardiac cycles. Non-limiting examples of representations of stethoscope data 506 can be found at FIGS. 4A and 4B. In some embodiments, stethoscope component 502 can be an electronic stethoscope (e-stethoscope) that comprises an amplifier to amplify sound wave signals and/or an electronic visible stethoscope that can comprise an optical sensor.

In some embodiments, stethoscope component 502 can be calibrated and/or can be configured to be calibrated using a calibration component 522. Calibration component 522 can comprise an accelerometer 524, which can be operatively coupled to a mass 526. Mass 526 can include or be operatively coupled to accelerometer 524. Mass 526 can be placed on the chest of the patient over or near heart 504. When the aortic valve 304 opens, producing a pressure wave, mass 526 will typically be accelerated. Hence, even if cases exist in which the tricuspid valve 306 closure does not sufficiently coincide with opening of the aortic valve 304, the calibration of the stethoscope component 504 can be employed to effectively tailor stethoscope component 502 to each individual patient.

In some embodiments, mass 526 can include or be operatively coupled to a strain gauge (not shown) instead of or in addition to being coupled to the accelerometer 524. In some embodiments, the calibration of stethoscope component 502 can be accomplished by employing a ballistocardiogram (BCG) device (not shown). The BCG device can be used in conjunction with the accelerometer 524 or the strain gauge. For example, the BCG device can measure a reaction force of the body to ejection of blood from the heart 504 to the vasculature. The time of opening of the aortic valve 304 can, in some embodiments, be assumed to be the same as the start of a BCG curve generated by the BCG device.

In some embodiments, system 500 can further comprise PPG (e.g., photoplethymography) component 510. The PPG component 510 can monitor a pressure wave of an extremity 512. In some embodiments, PPG component 510 can be an oximeter such as a pulse oximeter. A pulse oximeter, in some embodiments, can operate by illuminating the skin at extremity 512 and measuring light absorption characteristics. Such can be employed to monitor the perfusion of blood to the dermis and subcutaneous tissue of the skin.

In various embodiments, the extremity 512 of the patient can be any suitable portion of the patient including, but not limited to, wrist, hand, finger, ear, feet, or any other suitable location or area. Because some embodiments of the disclosed subject matter relate to persistent, on-going monitoring, PPG component 510, as well as other elements or components detailed herein, can be implemented in the form of a wearable device or object such as a bracelet, watch, ring, earring, shoe, headband, or other jewelry, apparel, and so forth. In some embodiments, PPG component 510 and/or stethoscope component 502 can comprise a transmitter or transceiver that can transmit or receive data wirelessly or via a wired connection.

Based on monitoring of extremity 512, PPG component 510 can generate PPG data 514. PPG data 514 can be representative of a pulse at extremity 512. In some embodiments, PPG data 514 can take the form of radial artery pulse wave of FIGS. 1 and 2. For example, PPG data can identify when the pressure wave, which begins when aortic valve 304 opens, reaches extremity 512.

System 500 can further comprise analysis component 508. Analysis component 508 can receive the stethoscope data 506 and/or PPG data 514. Analysis component 508 can determine, based on stethoscope data 506, a first time 516 corresponding to closure of a tricuspid valve 306 of heart 504. For example, analysis component 508 can analyze the sound pattern recorded by stethoscope component 502 to identify the pattern that matches the tricuspid valve 306 closing. First time 516 can be exemplified in some embodiments as $T_S$ of FIGS. 4A and 4B. Analysis component 508 can also determine a second time 518 corresponding to the pulse at extremity 512 based on PPG data 514. For example, PPG component 510 can detect when the BP wave arrives at extremity 512. Furthermore, analysis component 508 can determine PIT 520 as a function of first time 516 and second time 518.

In some embodiments, analysis component 508 can determine that an opening of an aortic valve 304 of heart 504 coincides with the closure of the tricuspid valve 306 of heart 504. In other words, analysis component 508 can determine that both the opening of the aortic valve 304 and the closing of the tricuspid valve 306 occur at first time 516. Such can be based on an assumed relationship between the valves or operation of the heart 504 or based on other data received by analysis component 508. For example, because it can be assumed that tricuspid valve 306 closure that can be detected by stethoscope component 502 coincides with aortic valve 304 opening, then first time 516 can be used as an accurate basis for determining PTT 520. In some cases, first time 516 (e.g., a time of tricuspid valve 306 closing) can be more accurate than data from an ECG, as detailed herein.

In some embodiments, stethoscope component 502, PPG component 510, and/or analysis component 508 can comprise a timer element. Illustrative examples can be found with reference to timers 528A, 528B, and 528C, which can be included in or operatively or communicatively coupled to stethoscope component 502, PPG component 510, and analysis component 508, respectively. While the term "timer" is employed herein, in various embodiments, the component can be or include a clock or other device configured to determined a time that an event or action occurs or that data or a signal is received. All such embodiments are envisaged.

In some embodiments, stethoscope component 502 can encode time information from timer 528A into stethoscope data 506. Similarly, PPG component 510 can encode time information from timer 528A into PPG data 514. Additionally or alternatively, analysis component 508 can employ time information from timer 528C to determine a correspondence between stethoscope data 506 and PPG data 514. Such information can be employed to compare stethoscope data 506 and PPG data 514, for instance to determine or identify temporal correspondence between stethoscope data 506 and PPG data 514. In some embodiments, all timers 528A, 528B, 528C can be synchronized.

Figure 6:
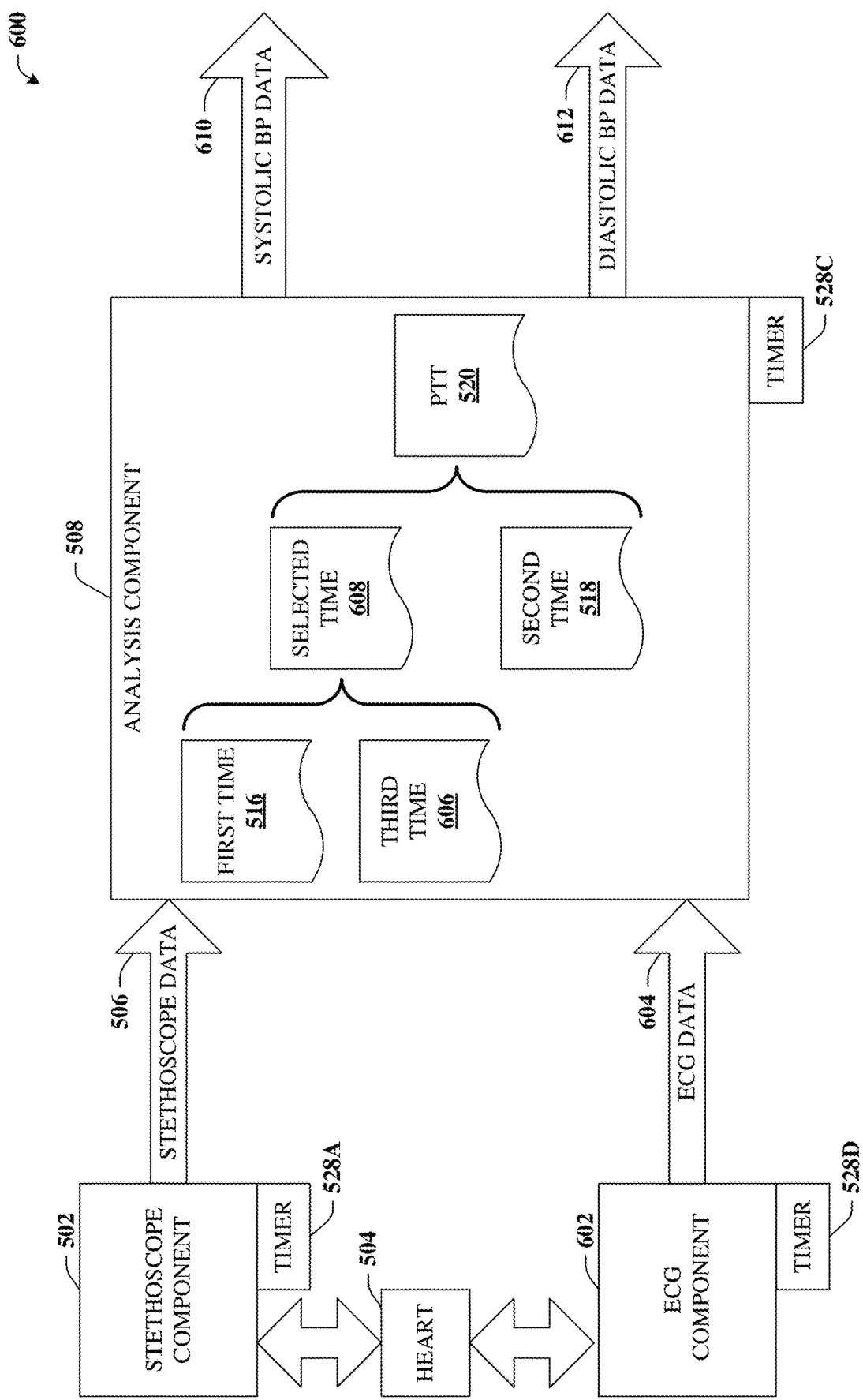
FIG. 6 illustrates another non-limiting example of a block diagram of a system that can facilitate determination of PIT or blood pressure (BP) in accordance with one or more embodiments described herein.

With reference now to FIG. 6, system 600 is provided. FIG. 6 illustrates another non-limiting example of a block diagram of a system that can facilitate determination of PIT or BP in accordance with one or more embodiments described herein. Repetitive description of like elements employed in other embodiments described herein is omitted for sake of brevity.

For example, in some embodiments, analysis component 508 can utilize data from both stethoscope component 502 and ECG component 602, both of which can be operable to monitor heart 504, albeit in different ways. For instance, as detailed, stethoscope component 502 can monitor mechanical signals such as sound, whereas ECG component 602 can monitor electrical signals such as effects due to depolarization of ventricle muscles of heart 504.

In addition to receiving stethoscope data 506 and PPG data 514 as discussed with reference to FIG. 5, analysis component 508 can, in some embodiments, receive ECG data 604 from ECG component 602. ECG data can be representative of an electrical charge in response to depolarization of heart 504. A non-limiting example representation of ECG data 604 can be ECG wave data 135 discussed with reference to FIGS. 1 and 2. Based on ECG data 604, analysis component 508 can determine third time 606. Third time 606 can correspond to an opening of the aortic valve as determined based on R peak (e.g., $R_P$ of FIG. 1) of ECG data 604. Generally, R peak represents a peak value recorded during a QT interval of the ECG data 604 where R, Q and T are labeled points of an ECG and the interval from point Q to point T is the QT interval. In some embodiments, ECG component 602 can comprise timer 528D, which can be substantially similar in structure and/or function to timers 528A, 528B, 528C discussed with reference to FIG. 5.

As has been discussed, for a normally functioning heart, R peak tends to have a consistent offset with, and tends to be a reliable indicator of, opening of the aortic valve 304. Thus, first time 516 and third time 606 will typically coincide with one another for a normally functioning heart. Thus, analysis component 508 can, in some cases, determine FI 520 as a function of third time 606 and second time 518 (and such is illustrated by selected time 608). Accordingly, F 520 can be determined as a function of selected time 608, which can be representative of either first time 516 determined from stethoscope data 506 or third time 606 determined from ECG data 604. In some embodiments, selected time 608 can be average value or other combination of first time 516 and third time 606.

In some embodiments, it is possible that first time 516 and third time 606 are the same or are substantially the same. In such cases, analysis component 508 can determine FI 520 using third time 606 in response to a determination that no deviation between first time 516 and third time 606 exists. Additionally or alternatively, analysis component 508 can determine F 520 using first time 516 in response to a determination that no deviation between first time 516 and third time 606 exists. Further detail in connection with determining whether a deviation exists is discussed with reference to FIG. 7.

In other embodiments, due to a variety of factors such as an aortic regurgitation and/or monitoring conditions, it is possible that first time 516 and third time 606 diverge and selected time 608 can be determined based on a default setting or based on a defined condition including, but not limited to, calibration condition, a patient condition, patient data, or environmental conditions. For example, one reason first time 516 and third time 606 diverge may be due to an aortic regurgitation or another condition that causes R peak of ECG data 604 to be an inaccurate indicator of aortic valve 304 opening. In such situations, the use of stethoscope data 506 for determination of P can be favored over ECG data 604.

Regardless of how F 520 is determined, in some embodiments, analysis component 508 can determine a systolic BP data 610 as a function of F 520. Systolic BP data 610 can be a measurement or estimation of a patient systolic BP. For example, in some embodiments, systolic BP can be represented as a natural log of the inverse of the square of PI 520. As one example, systolic BP can be $a*\ln(b/T^2)$. In some embodiments, "a" and "b" can be constants. In some embodiments "b" can reflect a constant that is a function of blood density, blood vessel radius, length of an artery, thickness of an artery, or similar. As another example, in some embodiments, systolic blood pressure can be $a*\ln(1/IT^2)+c$, where "a" and "c" can be constants.

Furthermore, in some embodiments, analysis component 508 can determine diastolic BP data 612 as a function of systolic BP data 610 and a fourth time. It is understood that diastolic BP data 612 can be a measurement or estimation of a patient diastolic BP. The fourth time can be representative of a time between radial artery pulse waves. In some embodiments, one example of the fourth time can be $T_2$ 197 of FIG. 2. In various embodiments, the fourth time can be employed to determine diastolic BP. For example, in some embodiments, diastolic BP can be $Kb+2/0.0031 \ln(Kc/PPD)-\frac{1}{3}*Ka/PPD^2$, where Ka, Kb, and Kc can be constants or other parameters determined based on a calibration procedure and where PPD can represent a peak-to-peak time in a pulse wave, which can also be referred to as a pulse percussion diastolic.

Figure 7:
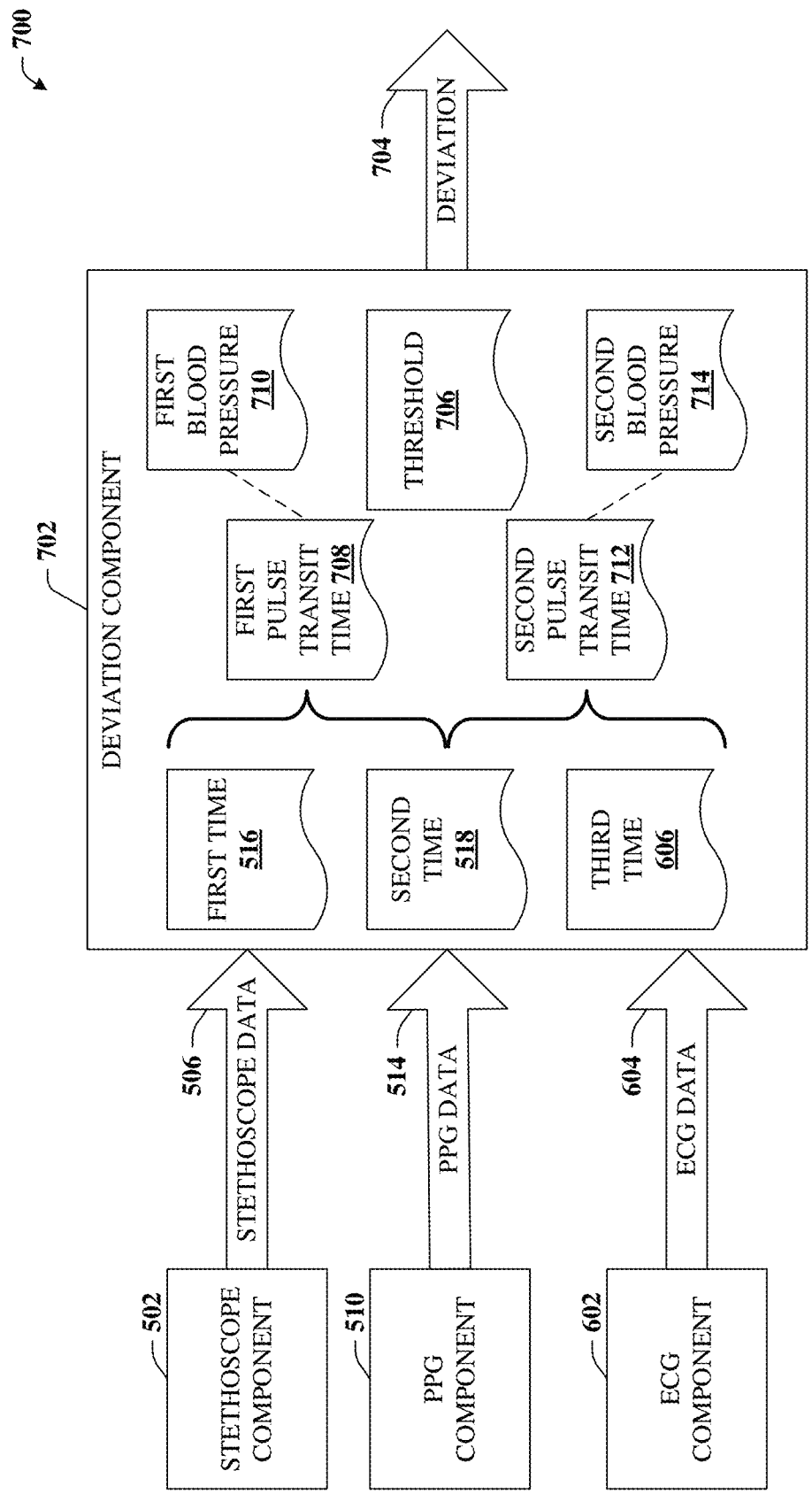
FIG. 7 illustrates a non-limiting example of a block diagram of a system that can facilitate determination or inference that a deviation exists between an aortic valve opening and an estimated opening determined based on the R peak of ECG data in accordance with one or more embodiments described herein.

Turning now to FIG. 7, system 700 is provided. FIG. 7 illustrates a non-limiting example of a block diagram of a system that can facilitate determination or inference that a deviation exists between an aortic valve opening determined based on R peak of ECG data in accordance with one or more embodiments described herein. Repetitive description of like elements employed in other embodiments described herein is omitted for sake of brevity.

System 700 can include deviation component 702. In some embodiments, deviation component 702 can be included in analysis component 508. Deviation component 702 can, for example, determine a deviation 704 in response to a determination that an opening of an aortic valve 304 of the heart 504 does not correspond to a time of aortic valve opening estimated from the R peak of the ECG data. In some embodiments, deviation component 702 can make such determination in response to receiving all or a portion of stethoscope data 506, PPG data 514, and/or ECG data 604, which can be respectively utilized to calculate first time 516, second time 518, and/or third time 606. In some embodiments, deviation component 702 can receive data indicative of first time 516, second time 518, and/or third time 606, for example, from analysis component 508. While FIG. 7 shows the stethoscope component 502 and PPG data 514, in other embodiments, the various data can be received from the analysis component in lieu of or in addition to the stethoscope component 502 and/or PPG data 514. All such embodiments are envisaged.

In some embodiments, deviation component 702 can determine deviation 704 in response to a determination that first time 516 differs from third time 606 by a defined threshold 706. In some embodiments, defined threshold 706 can be indicative of a difference in BP calculations that results between using, on the one hand, stethoscope data 506, and, on the other hand, using ECG data 604. For example, using stethoscope data 506 can result in a determination of first time 516. First time 516 can be used to determine first PIT 708, which, in turn can be used to calculate first BP 710. Conversely, using ECG data 604 can result in a determination of third time 606. Third time 606 can be used to determine second FI 712. Second F 712 can be utilized to determine second BP 714.

As discussed, when first time 516 deviates from third time 606, subsequent FI and BP determinations can also deviate. For example, first BP 710 and second BP 714 will be different and therefore represent a deviation. Hence, in embodiments where defined threshold 706 relates to a threshold difference between first time 516 and third time 606, defined threshold 706 can be selected such that the time difference varies by an amount that will result in a defined difference between first BP 710 and second BP 714. Thus, defined threshold 706 can be specified in units of time or in units of BP calculations. For example, in some embodiments, defined threshold 706 can represent a difference of at least about 8 millimeters (mm) of mercury (Hg) between first BP 710 determined based on first time 516 and second BP 714 determined based on third time 606. An 8 mm Hg difference can, in some implementations be appropriate as such conforms to certain standards of governmental bodies tasked with protecting public health and safety.

In other implementations, however, much higher standards can be maintained. For example, in some embodiments, defined threshold 706 can represent a difference of about 2 mm Hg between first BP 710 determined based on first time 516 and second BP 714 determined based on third time 606. Other values for defined threshold 706 are contemplated, and such can be configurable based on implementation or application. While various numerical values are used in the application, it is understood that such values are mere examples and other values can also be employed, as appropriate. All such embodiments are envisaged.

Figure 8:
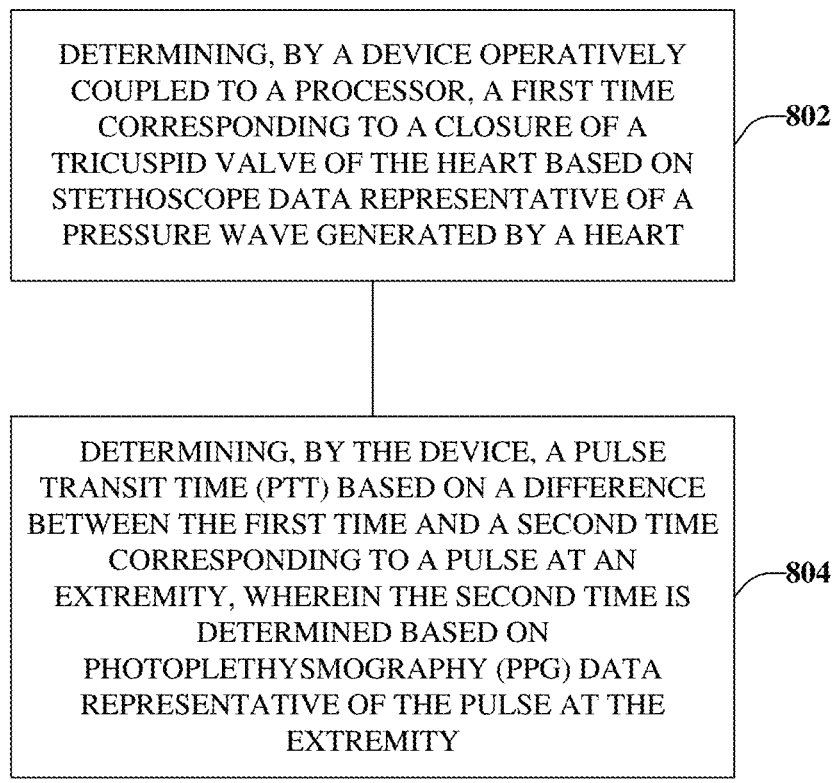
FIG. 8 illustrates a flow diagram of an example, non-limiting computer-implemented method to determine PTT based on stethoscope data in accordance with one or more embodiments described herein.
Figure 9:
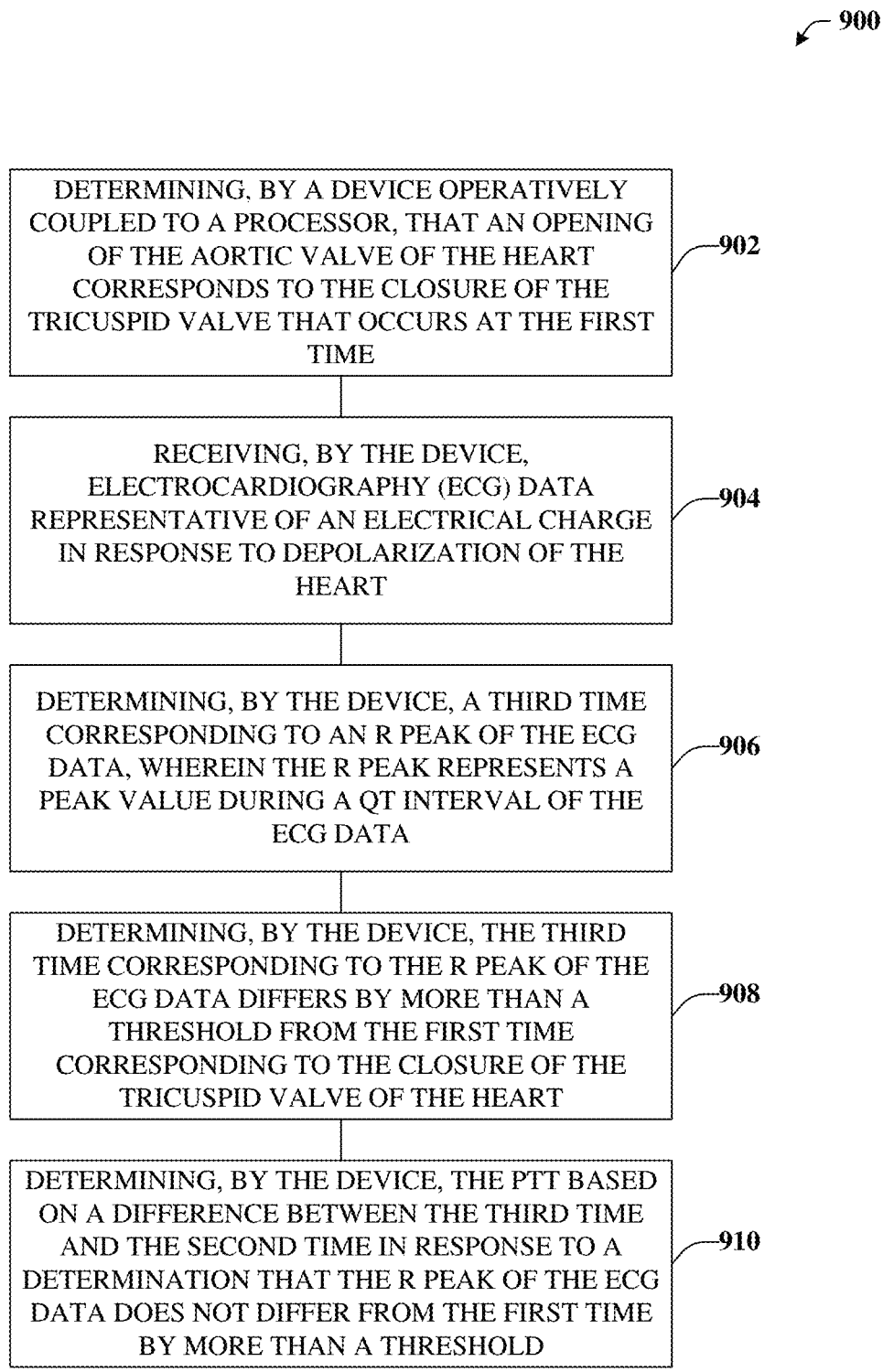
FIG. 9 illustrates a flow diagram of an example, non-limiting computer-implemented method to determine PTT based on stethoscope data in accordance with one or more embodiments described herein.

FIGS. 8-9 illustrate various methodologies in accordance with the disclosed subject matter. While, for purposes of simplicity of explanation, the methodologies are shown and described as a series of acts, it is to be understood and appreciated that the disclosed subject matter is not limited by the order of acts, as some acts can occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts can be required to implement a methodology in accordance with the disclosed subject matter. Additionally, it should be further appreciated that the methodologies disclosed hereinafter and throughout this specification are capable of being stored on an article of manufacture to facilitate transporting and transferring such methodologies to computers.

FIG. 8 illustrates a flow diagram of an example, non-limiting computer-implemented method 800 to determine PIT based on stethoscope data in accordance with one or more embodiments described herein. Repetitive description of like elements employed in other embodiments described herein is omitted for sake of brevity.

At reference numeral 802, a device (e.g., analysis component 508) operatively coupled to a processor can determine a first time corresponding to a closure of a tricuspid valve of a heart. Determining that the first time corresponds to the closure of the tricuspid valve can be based on stethoscope data representative of a mechanical wave generated by the heart. In some embodiments, the stethoscope data can be determined by and/or received from a stethoscope device (e.g., stethoscope component 502), which can be a wearable device that can be worn or employed by a patient such as an electronic stethoscope, an electronic visible stethoscope, or the like.

At reference numeral 804, the device can determine a PIT. The PTT can be determined based on a difference between the first time and a second time corresponding to a pulse wave at an extremity. The second time can be determined based on PPG data representative of the pulse wave at the extremity. In some embodiments, the PPG data can be determined by and/or received from a PPG device (e.g., PPG component 510). In some embodiments, the PPG device can be a pulse oximeter. In some embodiments, the extremity can be a patient's finger, ear, wrist, foot, or substantially any portion of the patient operable to a suitable portion of the arterial tree.

FIG. 9 illustrates a flow diagram of an example, non-limiting computer-implemented method to determine PTT based on stethoscope data in accordance with one or more embodiments described herein. Repetitive description of like elements employed in other embodiments described herein is omitted for sake of brevity.

At reference numeral 902, the device (e.g., analysis component 508) can determine that an opening of an aortic valve of the heart corresponds to the closure of the tricuspid valve that occurs at the first time. Thus, the closure of the tricuspid valve that can be detected by the stethoscope component and/or readily identified from the stethoscope data can be determined or inferred to correspond to and/or occur at substantially the same time as opening of the aortic valve.

At reference numeral 904, the device can receive electrocardiography (ECG) data representative of an electrical charge in response to depolarization of the heart. At reference numeral 906, the device can determine a third time corresponding to an opening of the aortic valve determined based on R peak of the ECG data. The R peak can represent a peak value during a QT interval of the ECG data. As has been detailed, either one of the first time and the third time can be used to represent an opening of the aortic valve, which can represent a start time for determining PT.

At reference numeral 908, the device can determine the third time corresponding to opening of the aortic valve determined based on the R peak of the ECG data differs by more than a threshold from the first time corresponding to the closure of the tricuspid valve of the heart. In other words, the device can determine if there is a divergence or deviation between two independent techniques for estimating the opening of the aortic valve. If this deviation is sufficient such as differing by more than the threshold, F can be determined based on the first time that is derived from the stethoscope data.

On the other hand, if the deviation is not sufficient such as not differing by more than the threshold, F can be determined based on the third time that is derived from ECG data. For example, at reference numeral 910, the device can determine the F based on a difference between the third time and the second time in response to a determination that opening of the aortic valve determined based on the R peak of the ECG data does not differ from the first time by more than a threshold.

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 10, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 10:
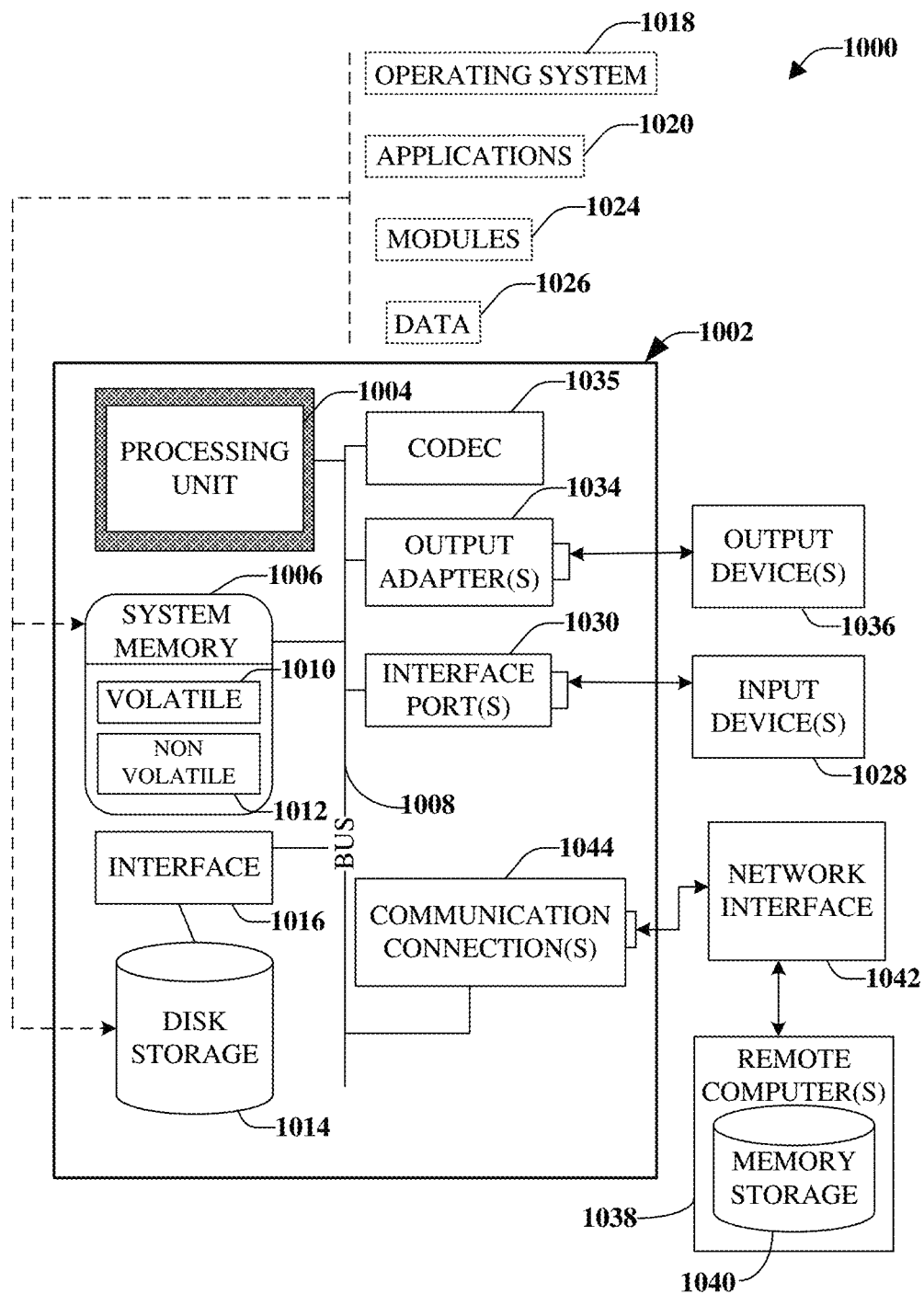
FIG. 10 illustrates a block diagram of an example, non-limiting operating environment in which one or more embodiments described herein can be facilitated.

With reference to FIG. 10, an example environment 1000 for implementing various aspects of the claimed subject matter includes a computer 1002. The computer 1002 includes a processing unit 1004, a system memory 1006, a codec 1035, and a system bus 1008. The system bus 1008 couples system components including, but not limited to, the system memory 1006 to the processing unit 1004. The processing unit 1004 can be any of various available processors. Dual microprocessors and other multiprocessor architectures also can be employed as the processing unit 1004.

The system bus 1008 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1006 includes volatile memory 1010 and non-volatile memory 1012, which can employ one or more of the disclosed memory architectures, in various embodiments. The basic input/output system (BIOS), containing the basic routines to transfer information between elements within the computer 1002, such as during start-up, is stored in non-volatile memory 1012. In addition, according to present innovations, codec 1035 can include at least one of an encoder or decoder, wherein the at least one of an encoder or decoder can consist of hardware, software, or a combination of hardware and software. Although, codec 1035 is depicted as a separate component, codec 1035 can be contained within non-volatile memory 1012. By way of illustration, and not limitation, non-volatile memory 1012 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1012 can employ one or more of the disclosed memory devices, in at least some embodiments. Moreover, non-volatile memory 1012 can be computer memory (e.g., physically integrated with computer 1002 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1010 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1002 can also include removable/non-removable, volatile/non-volatile computer storage medium. FIG. 10 illustrates, for example, disk storage 1014. Disk storage 1014 includes, but is not limited to, devices like a magnetic disk drive, solid state disk (SSD), flash memory card, or memory stick. In addition, disk storage 1014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1014 to the system bus 1008, a removable or non-removable interface is typically used, such as interface 1016. It is appreciated that storage devices 1014 can store information related to a user. Such information might be stored at or provided to a server or to an application running on a user device. In one embodiment, the user can be notified (e.g., by way of output device(s) 1036) of the types of information that are stored to disk storage 1014 or transmitted to the server or application. The user can be provided the opportunity to opt-in or opt-out of having such information collected or shared with the server or application (e.g., by way of input from input device(s) 1028).

It is to be appreciated that FIG. 10 describes software that acts as an intermediary between users and the basic computer resources described in the suitable operating environment 1000. Such software includes an operating system 1018. Operating system 1018, which can be stored on disk storage 1014, acts to control and allocate resources of the computer system 1002. Applications 1020 take advantage of the management of resources by operating system 1018 through program modules 1024, and program data 1026, such as the boot/shutdown transaction table and the like, stored either in system memory 1006 or on disk storage 1014. It is to be appreciated that the claimed subject matter can be implemented with various operating systems or combinations of operating systems.

A user enters commands or information into the computer 1002 through input device(s) 1028. Input devices 1028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1004 through the system bus 1008 via interface port(s) 1030. Interface port(s) 1030 include, for example, a serial port, a parallel port, a game port, and a universal serial bus (USB). Output device(s) 1036 use some of the same type of ports as input device(s) 1028. Thus, for example, a USB port can be used to provide input to computer 1002 and to output information from computer 1002 to an output device 1036. Output adapter 1034 is provided to illustrate that there are some output devices 1036 like monitors, speakers, and printers, among other output devices 1036, which require special adapters. The output adapters 1034 include, by way of illustration and not limitation, video and sound cards that provide a means of connection between the output device 1036 and the system bus 1008. It should be noted that other devices or systems of devices provide both input and output capabilities such as remote computer(s) 1038.

Computer 1002 can operate in a networked environment using logical connections to one or more remote computers, such as remote computer(s) 1038. The remote computer(s) 1038 can be a computer, a server, a router, a network PC, a workstation, a microprocessor based appliance, a peer device, a smart phone, a tablet, or other network node, and typically includes many of the elements described relative to computer 1002. For purposes of brevity, only a memory storage device 1040 is illustrated with remote computer(s) 1038. Remote computer(s) 1038 is logically connected to computer 1002 through a network interface 1042 and then connected via communication connection(s) 1044. Network interface 1042 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1044 refers to the hardware/software employed to connect the network interface 1042 to the bus 1008. While communication connection 1044 is shown for illustrative clarity inside computer 1002, it can also be external to computer 1002. The hardware/software necessary for connection to the network interface 1042 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   an electrocardiogram (ECG) sensor comprising electrocardiogram circuitry, electrodes and wiring, wherein the electrodes detect electrical changes on skin of a patient that occur in response to a muscle electrophysiological pattern of a heart of the patient, and wherein the ECG circuitry generates wave data to describe the electrical changes; and
   a processor that:
   determines a first time corresponding to a closure of a tricuspid valve of a heart based on stethoscope data representative of a mechanical wave generated by the heart, wherein the stethoscope data is obtained via a stethoscope component that evaluates one or more mechanical waves to estimate timing during which an aortic valve is open;
   determines a second time corresponding to a pulse wave at an extremity, wherein the second time is determined based on photoplethysmography data representative of the pulse wave at the extremity; and
   determines a third time corresponding to opening of the aortic valve determined based on whether the R peak time of ECG data differs by more than a defined threshold from the first time corresponding to the closure of the tricuspid valve of the heart,
   wherein the system determines if there is a deviation between two independent techniques for estimating the opening of the aortic valve and:
   wherein if the deviation differs by more than the defined threshold, the processor determines the pulse transit time (PTT) based on a difference between the first time that is derived from the stethoscope data and the second time corresponding to the pulse wave at the extremity, and
   wherein if the deviation does not differ by more than the defined threshold, the processor determines the PTT based on a difference between the third time that is derived from ECG data and the second time corresponding to the pulse wave at the extremity.

2. The system of claim 1, wherein the processor also facilitates receipt of electrocardiography data representative of an electrical charge generated based on depolarization of the heart.

3. The system of claim 1, wherein the defined threshold represents a difference of at least about 8 millimeters of mercury between a first blood pressure calculation determined at a first time and a second blood pressure calculation determined at a second time.

4. The system of claim 1, wherein the defined threshold represents a difference of at least about 2 millimeters of mercury between a first blood pressure calculation determined at a first time and a second blood pressure calculation determined at a second time.

5. The system of claim 1, wherein the processor also determines a diastolic blood pressure measurement as a function of a systolic blood pressure measurement or a time between radial artery pulse waves.

6. A computer program product for determining a pulse transit time, the computer program product comprising a computer readable storage medium having program instructions embodied therewith, the program instructions executable by a processor to cause the processor to:
   determine, by the processor, a first time corresponding to a closure of a tricuspid valve of a heart based on stethoscope data representative of a mechanical wave generated by the heart, wherein the stethoscope data is obtained via a stethoscope component that evaluates one or more mechanical waves to estimate timing during which an aortic valve is open;
   determine, by the processor, a second time corresponding to a pulse wave at an extremity, wherein the second time is determined based on photoplethysmography data representative of the pulse wave at the extremity, and wherein electrodes of the ECG sensor comprising electrocardiogram circuitry, the electrodes and wiring detect electrical changes on skin of a patient that occur in response to a muscle electrophysiological pattern of the heart of the body, and wherein the ECG circuitry generates wave data to describe the electrical changes; and determine, by the processor, a third time corresponding to opening of the aortic valve determined based on whether the R peak time of ECG data differs by more than a defined threshold from the first time corresponding to the closure of the tricuspid valve of the heart, wherein the processor determines if there is a deviation between two independent techniques for estimating the opening of the aortic valve and:

wherein if the deviation differs by more than the defined threshold, the processor determines the pulse transit time (PTT) based on the first time that is derived from the stethoscope data and the second time corresponding to the pulse wave at the extremity, and wherein if the deviation does not differ by more than the defined threshold, the processor determines the PTT based on a difference between the third time that is derived from ECG data and the second time corresponding to the pulse wave at the extremity.

7. The computer program product of claim 6, wherein program instructions are also executable by the processor to facilitate receipt of electrocardiography data representative of an electrical charge generated based on depolarization of the heart.

8. The computer program product of claim 6, wherein the program instructions are also executable by the processor to determine a deviation in response to a determination that the aortic valve opening fails to correspond to R peak of the electrocardiography data.

9. The computer program product of claim 6, wherein the defined threshold represents a difference of at least about 8 millimeters of mercury between a first blood pressure calculation determined at a first time and a second blood pressure calculation determined at a second time.

10. The computer program product of claim 6, wherein the defined threshold represents a difference of at least about 2 millimeters of mercury between a first blood pressure calculation determined at a first time and a second blood pressure calculation determined at a second time.

11. The computer program product of claim 6, wherein the program instructions are also executable by the processor to determine a diastolic blood pressure measurement as a function of a systolic blood pressure measurement or a time between radial artery pulse waves.

* * * * *